(12) United States Patent
Tachibana et al.

(10) Patent No.: US 9,475,052 B2
(45) Date of Patent: Oct. 25, 2016

(54) MICROFLUIDIC DEVICE (71) Applicant: PANASONIC INTELLECTUAL PROPERTY MANAGEMENT CO., LTD., Osaka (JP)

(72) Inventors: Hiroaki Tachibana, Osaka (JP); Koji Tsuji, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 188 days.

(21) Appl. No.: 14/408,433

(22) PCT Filed: Mar. 4, 2013

(86) PCT No.: PCT/JP2013/001323
§ 371 (c)(1),
(2) Date: Dec. 16, 2014

(87) PCT Pub. No.: WO2013/190745
PCT Pub. Date: Dec. 27, 2013

(65) Prior Publication Data
US 2015/0190811 A1 Jul. 9, 2015

(30) Foreign Application Priority Data
Jun. 22, 2012 (JP) ................. 2012-140563

(51) Int. Cl.
*B01J 19/00* (2006.01)
*B01L 7/00* (2006.01)
(Continued)

(52) U.S. Cl.
CPC ............ *B01L 7/525* (2013.01); *B01J 19/0093* (2013.01); *B01L 3/5027* (2013.01);
(Continued)

(58) Field of Classification Search
CPC .............. B01J 19/0093; B01J 19/2485; B01J 2219/00783; B01J 2219/00822; B01J 2219/00873; B01J 2219/00876; B01J 2219/00885; B01J 2219/00081; B01L 2300/0816; B01L 2300/087; B01L 2300/0883
See application file for complete search history.

(56) References Cited

U.S. PATENT DOCUMENTS 6,440,725 B1   8/2002   Pourahmadi et al.
6,893,879 B2   5/2005   Petersen et al.
(Continued)

FOREIGN PATENT DOCUMENTS

CN   1907555 A    2/2007
CN   101086009 A  12/2007
(Continued)

OTHER PUBLICATIONS

International Search report from PCT/JP2013/001323, with English language translation, mail date is May 28, 2013.
(Continued)

*Primary Examiner* — Jennifer Wecker
(74) *Attorney, Agent, or Firm* — Greenblum & Bernstein, P.L.C.

(57) ABSTRACT

The present invention provides a miniaturized microfluidic device with a heater that has a simple structure without needing adhesion means for improving the heat transfer between the heater block and the device, and which can form the uniform temperature regions. Disclosed is a microfluidic device, including: a substrate; a reaction flow path formed on the substrate; and a temperature adjustment heater for heating the reaction flow path, in which a reaction flow path formation region including the reaction flow path formed therein and a temperature adjustment heater formation region including the temperature adjustment heater formed therein are alternately arranged on the substrate, the reaction flow path is formed to be bent at least one time in the reaction flow path formation region, and the temperature adjustment heater is formed to be bent at least one time in the temperature adjustment heater formation region.

15 Claims, 8 Drawing Sheets

(51) Int. Cl.
  *F24J 1/00*    (2006.01)
  *F28D 7/00*    (2006.01)
  *B01L 3/00*    (2006.01)
  *C12M 1/26*    (2006.01)
  *F28D 3/00*    (2006.01)
  *F28D 5/00*    (2006.01)
  *C12M 3/00*    (2006.01)
  *H01L 23/473*  (2006.01)
  *B01J 19/24*   (2006.01)
  *B01J 37/02*   (2006.01)

(52) U.S. Cl.
  CPC ....... *B01L 3/502715* (2013.01); *C12M 33/00* (2013.01); *B01J 19/2485* (2013.01); *B01J 37/0228* (2013.01); *B01J 2219/00081* (2013.01); *B01J 2219/00783* (2013.01); *B01J 2219/00822* (2013.01); *B01J 2219/00873* (2013.01); *B01J 2219/00876* (2013.01); *B01J 2219/00885* (2013.01); *B01L 2300/087* (2013.01); *B01L 2300/0816* (2013.01); *B01L 2300/0883* (2013.01); *B01L 2300/1827* (2013.01)

(56)         References Cited

U.S. PATENT DOCUMENTS 7,569,346  B2    8/2009   Petersen et al.
  2002/0042125 A1  4/2002   Petersen et al.
  2005/0194316 A1  9/2005   Pourahmadi et al.
  2005/0266448 A1  12/2005  Hagiwara et al.
  2007/0048777 A1  3/2007   Hagiwara et al.
  2008/0206848 A1  8/2008   Hagiwara et al.
  2014/0220668 A1  8/2014   Tachibana et al.
  2014/0246625 A1* 9/2014   Tonkovich ............... B01J 37/18
                                                       252/373

FOREIGN PATENT DOCUMENTS

FR    WO 2004040645 A1 * 5/2004  ......... B01J 19/0093
  JP       2003-284943      10/2003
  JP       2004-191256       7/2004
  JP       2005-192554       7/2005
  JP       2005-295877      10/2005
  JP       2009-014736       1/2009
  WO       2004/040645       5/2004

OTHER PUBLICATIONS

Transmittal and English translation of Written Opinion of the International Searching Authority, mailed date Dec. 31, 2014.
Office Action and Search Report in Taiwanese Application No. 102107019 along with English translation of Search Report, mailed Mar. 10, 2015.

* cited by examiner

MICROFLUIDIC DEVICE

TECHNICAL FIELD

The present invention relates to microfluidic devices, such as a minute reaction device (microreactor), an integrated DNA device, or a minute electrophoresis device.

BACKGROUND ART

In recent years, microfluidic devices, such as a minute reaction device, an integrated DNA device, or a minute electrophoresis device, are manufactured by applying microfabrication techniques, and these microfluidic devices have been attracting attention. The microfluidic device includes a very narrow reaction flow path, in which a chemical reaction or the like occurs, and thus can very effectively analyze specimens at low cost.

Patent Document 1 discloses use of the microfluidic device as a method for changing a temperature of a reacting fluid at high speed in a reaction device for providing a desired change in temperature of the reacting fluid.

In the method disclosed in Patent Document 1, a device substrate is separated into a multiple of regions each having different temperature. Meandering flow paths are formed in the separated temperature regions to pass therethrough. Thus, the reacting fluid that travels through the flow paths has its temperature changed to a corresponding temperature in each temperature region. With such an arrangement, the fluid can have the desired changes in temperature only by allowing the fluid to flow through the meandering flow paths, which can achieve the high-speed change in temperature of the fluid.

Patent Document 1: JP 2005-192554 A

DISCLOSURE OF THE INVENTION

Problems to be Solved by the Invention

Figure 8A:
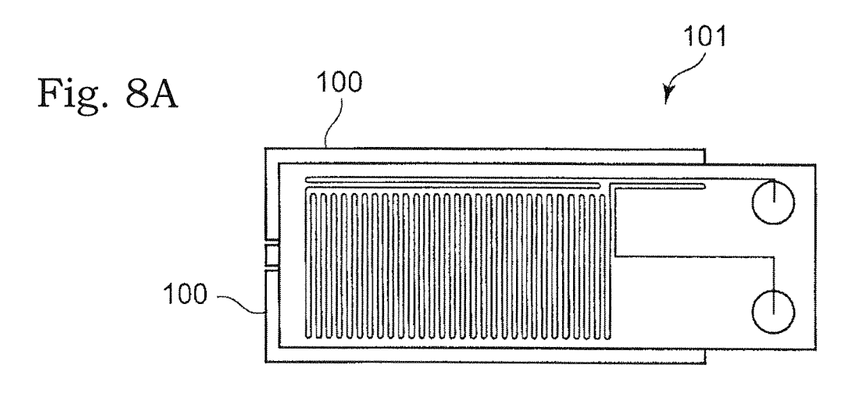
FIG. 8A is a top view of a conventional microfluidic device.
Figure 8B:
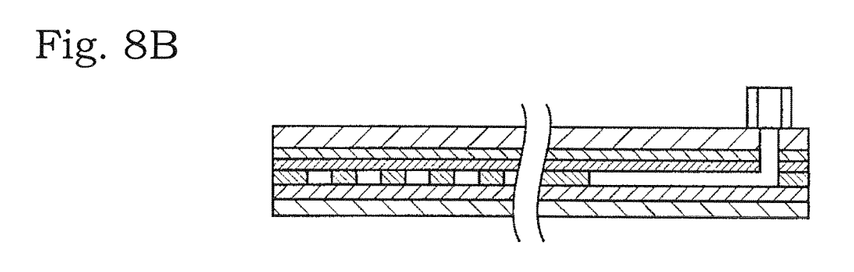
FIG. 8B is a cross-sectional view thereof.

However, in the conventional method disclosed in Patent Document 1, as shown in FIG. 8, a microfluidic device 101 is heated by a large-sized external heater block 100 attached to the outside of the microfluidic device 101, which poses the following problems: 1) the size of an entire system is increased by the size of the external heater block 10; and 2) an adhesion means between the heater block 100 and the microfluidic device 101 is required to improve heat transfer between the heater block 100 and the microfluidic device 101, leading to a complicated structure of the system.

Further, the heater block 100 causes uneven heating, thus making it difficult to uniformly heat the fluid in the reaction flow path.

The present invention has been made in view of the foregoing circumstances, and it is an object of the present invention to provide a miniaturized microfluidic device with a heater that has a simple structure and which can form uniform temperature regions.

Solution to Problem

In order to solve the foregoing problems, a microfluidic device according to the invention includes: a substrate; a reaction flow path formed on the substrate; and a temperature adjustment heater for heating the reaction flow path, in which a reaction flow path formation region including the reaction flow path formed therein and a temperature adjustment heater formation region including the temperature adjustment heater formed therein are alternately arranged on the substrate, the reaction flow path is formed to be bent at least one time in the reaction flow path formation region, and the temperature adjustment heater is formed to be bent at least one time in the temperature adjustment heater formation region.

The microfluidic device according to the invention further includes a first temperature region and a second temperature region, each having the reaction flow path formation region and the temperature adjustment heater formation region being alternately arranged in one direction therein, in which the first temperature region and the second temperature region are arranged side by side in a direction different from the one direction.

In the microfluidic device according to the invention, a first reaction flow path formation region included in the first temperature region and a second reaction flow path formation region included in the second temperature region are arranged in a staggered manner, and the reaction flow paths respectively formed in the first reaction flow path formation region and in the second reaction flow path formation region being located close to each other are formed to communicate with each other.

In the microfluidic device according to the invention, preferably, a first temperature adjustment heater formation region included in the first temperature region and a second temperature adjustment heater formation region included in the second temperature region are arranged in a staggered manner, and the temperature adjustment heaters respectively formed in the first temperature adjustment heater formation region and in the second temperature adjustment heater formation region being located close to each other are continuously formed.

Specifically, in the microfluidic device according to the invention, two or more temperature adjustment heaters each being bent to meander are preferably disposed in the one temperature adjustment heater formation region.

Likewise, in the microfluidic device according to the invention, two or more reaction flow paths each being bent to meander and separated are preferably disposed in the one reaction flow path formation region.

In the microfluidic device according to the invention, the number of bending the temperature adjustment heater in the one temperature adjustment heater formation region preferably ranges from 1 to 10.

Likewise, in the microfluidic device according to the invention, the number of bending the reaction flow path in the one reaction flow path formation region preferably ranges from 1 to 10.

The microfluidic device according to the invention preferably further includes a protective substrate over the substrate. The reaction flow path formed in the substrate to be opened outward, and the temperature adjustment heater disposed in the substrate are covered with the protective substrate.

The microfluidic device according to the invention may further include an isolation trench formed at a boundary between the two or more temperature regions to be opened at a back surface of the substrate.

The microfluidic device according to the invention may further include a through hole to penetrate the substrate from the back surface to a front surface thereof at the boundary.

Further, in the microfluidic device according to the invention, preferably, a stepped portion may be formed between a surface with the temperature adjustment heater formed thereon and the front surface of the substrate, so that the temperature adjustment heater does not protrude from the front surface of the substrate.

In the microfluidic device according to the invention, the temperature adjustment heater is preferably a metal thin film heater.

In the microfluidic device according to the invention, the temperatures of the two or more temperature adjustment heaters are preferably adjustable independently.

The above-mentioned microfluidic device according to the invention can be used as a polymerase chain reaction device.

Effects of the Invention

According to the microfluidic device of the invention, since the reaction flow path formation region including the reaction flow path being formed to be bent at least one time, and the temperature adjustment heater formation region including the temperature adjustment heater being formed to be bent at least one time are alternately arranged over the substrate, the uniform temperature regions can be formed therein. In particular, when a protruding part formed by bending the reaction flow path one time in the reaction flow path formation region, and a protruding part formed by bending the temperature adjustment heater one time in the temperature adjustment heater formation region are arranged in a nested pattern, the reaction flow path can be more uniformly heated by the temperature adjustment heater. The temperature adjustment heater formation region is formed over the substrate, which does not need any adhesion means for improving the heat transfer between a heater block and the microfluidic device, resulting in a simple structure of the microfluidic device. Further, since the temperature adjustment heater can be formed over the substrate by printing, for example, a thin metal film over the substrate without needing any other heater block, the microfluidic device can be reduced in size.

Accordingly, the present invention can provide a miniaturized microfluidic device with the heater that has a simple structure, and which can form uniform temperature regions.

MODE FOR CARRYING OUT THE INVENTION

Preferred embodiments for carrying out the invention will be described in detail with reference to the accompanying drawings. The embodiments mentioned below illustrate a microfluidic device to embody the technical idea of the invention, and are not intended to limit the scope of the invention. The dimension, material, shape, relative position, and the like of components mentioned in the embodiments are only illustrative rather than limiting the scope of the invention unless otherwise specified. In some drawings, the sizes and positional relationships of members may be emphasized to clarify the description below.

First Embodiment

Figure 1:
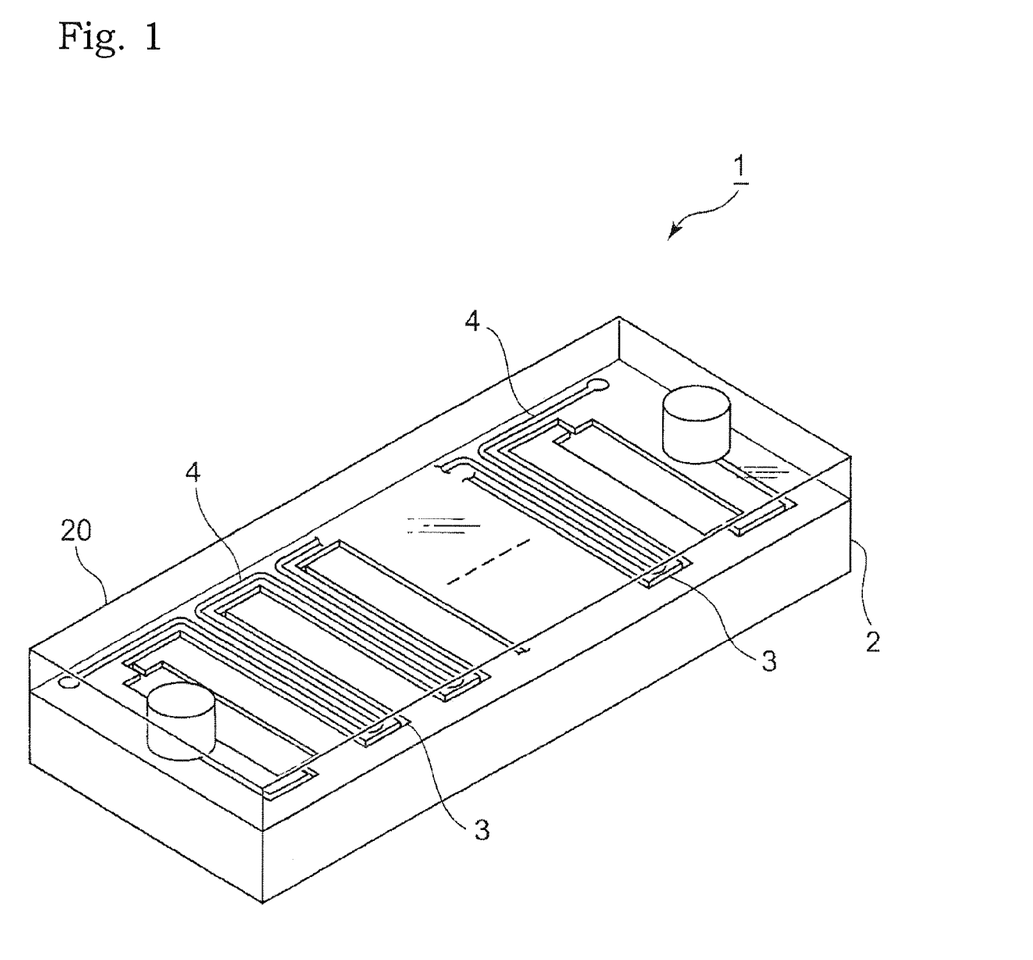
FIG. 1 is a perspective view of a microfluidic device according to a first embodiment of the invention.

FIG. 1 shows a perspective view of a microfluidic device 1 according to a first embodiment of the invention. As shown in FIG. 1, the microfluidic device 1 in the first embodiment includes a substrate 2, reaction flow paths 3 formed on the substrate 2, and temperature adjustment heaters 4 formed in the vicinity of the respective reaction flow paths 3 on the substrate 2 and adapted to heat the reaction flow paths 3.

Figure 2:
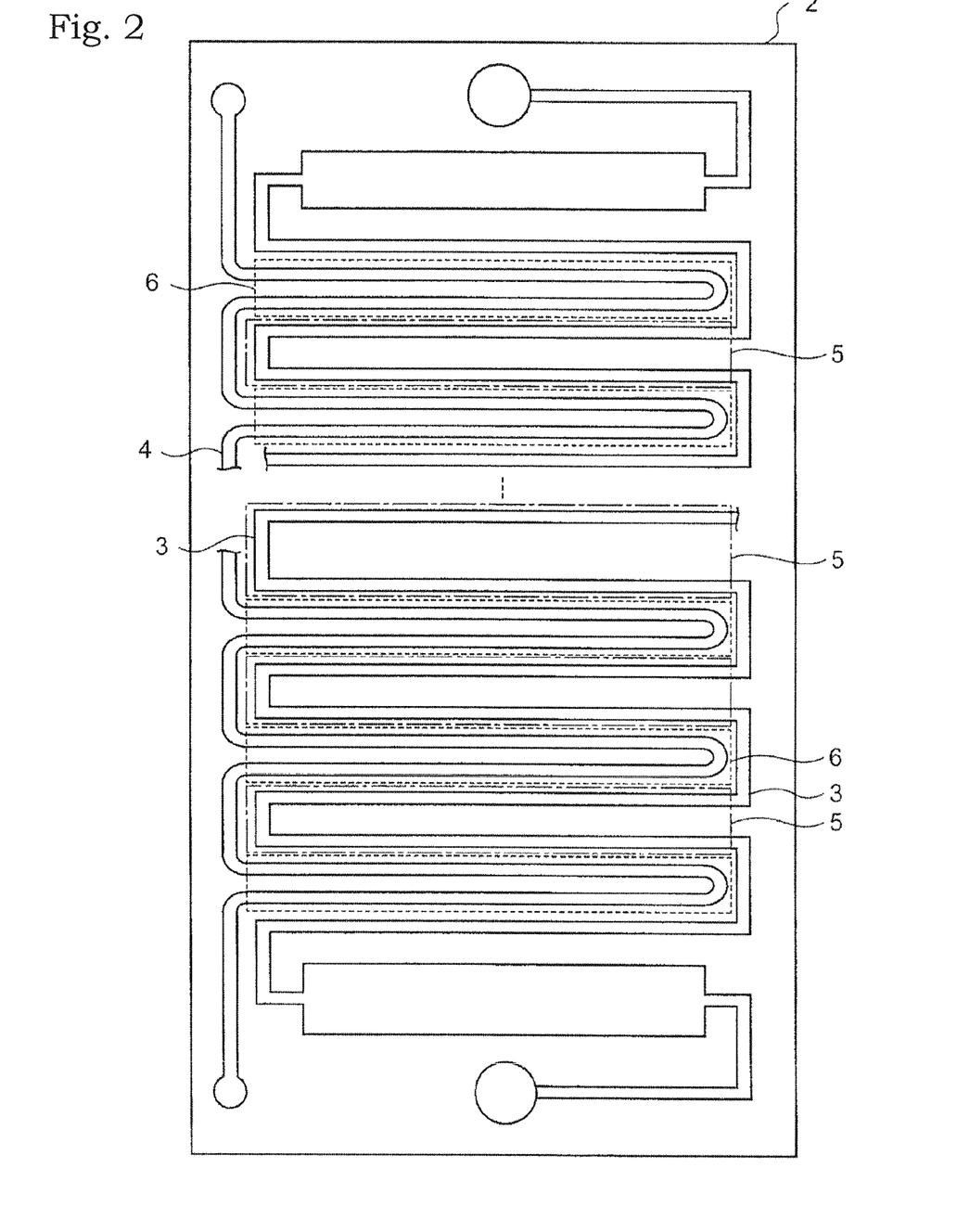
FIG. 2 is a top view of a substrate included in the microfluidic device in the first embodiment of the invention.

FIG. 2 shows a top view of the substrate 2 included in the microfluidic device 1 in the first embodiment of the invention. As shown in FIG. 2, reaction flow path formation regions 5 each having the reaction flow path 3 formed therein, and temperature adjustment heater formation regions 6 each having the temperature adjustment heater 4 formed therein are alternately arranged over the substrate 2 in one direction (in the longitudinal direction of the substrate in the first embodiment). Each temperature adjustment heater 4 is formed along and near the reaction flow path 3, so that the fluid or the like in the reaction flow path 3 can be uniformly heated by the temperature adjustment heater 4.

The shape in the top view of the reaction flow path 3 formed in the reaction flow path formation region 5 is not specifically limited to a substantially U-like shape shown in FIG. 2 or the like, but may be any other shape. Any of the reaction flow paths 3 may differ from other reaction flow paths 3 in shape, or may have the same shape as other reaction flow paths 2. However, these reaction flow paths preferably have the same shape in terms of uniform heat distribution. Thus, the fluid or the like passing through the reaction flow path 3 can be heated uniformly.

The reaction flow path 3 is preferably formed uniformly in the same reaction flow path formation region 5. The phrase "the reaction flow path 3 is preferably formed uniformly in the same reaction flow path formation region 5" as used herein means that the reaction flow path 3 is formed at an equal density within one of the reaction flow path formation regions 5.

The same goes for the shape in the top view of and the uniform formation of the temperature adjustment heater 4. Likewise, the temperature adjustment heater 4 is uniformly formed in the same temperature adjustment heater formation region 6, which can uniformly heat the reaction flow path 3, thus obtaining the uniform heat distribution.

The first embodiment will describe the case where the shapes in the top view of the reaction flow path 3 and the temperature adjustment heater 4 are protruding with bent parts thereof as a tip end (protruding part), by way of example.

In the first embodiment of the invention, at the reaction flow path formation region 5, as shown in FIG. 2, the reaction flow path 3 is bent at least one time or more to form the protruding shape. In this way, a protruding part is formed. The phrase "the reaction flow path 3 is bent to form" as used herein means that as shown in FIG. 2, the reaction flow path 3 linearly extends in one direction, turns back in one position in the direction opposite to the one direction (for example, in the direction at substantially 180° with respect to the one direction), and then linearly extends in the opposite direction. As shown in FIG. 2, the bent part may be one that discontinuously turns back (such that the gradient of a tangent at the tip end changes discontinuously) (that is, for example, in a substantially horizontal U-like shape (in a quadrilateral shape with one side thereof opened)), or may be one that is continuously curved modestly (such that the gradient of a tangent at the tip end changes continuously) (that is, for example, in a substantially vertical U-like shape). The number of bending the reaction flow path 3 is not limited to one time, and may be twice or more (for example, about 2 to 50 times).

Also in the temperature adjustment heater formation region 6, the temperature adjustment heater 4 is bent at least one time to form a protruding shape. Likewise, the phrase "the temperature adjustment heater 4 is bent to form" as used herein means that as shown in FIG. 2, the temperature adjustment heater 4 linearly extends in one direction, turns back in one position in the direction opposite to the one direction (for example, in the direction at substantially 180° with respect to the one direction), and then linearly extends in the opposite direction. The bent part may be one that discontinuously turns back (such that the gradient of a tangent at the tip end changes discontinuously) (that is, for example, in a substantially horizontal U-like shape (in a quadrilateral shape with one side thereof opened)), or may be one that has its tip end continuously curved modestly (such that the gradient of a tangent at the tip end changes continuously) (that is, for example, in a substantially vertical U-like shape) as shown in FIG. 2. The number of bending the temperature adjustment heater 4 is not limited to one time, and may be twice or more (for example, about 2 to 50 times).

When the temperature adjustment heater 4 includes two or more bent parts, and two or more protruding parts are formed, the protruding parts are connected together on the side opposite to the bent part to form the meandering temperature adjustment heater 4 as shown in FIG. 2.

As shown in FIG. 2, the term "protruding part" as used herein means a part that extends only by a predetermined length as mentioned above (which is substantially the same as the width of the formation region (reaction flow path formation region 5, temperature adjustment heater formation region 6) in the longitudinal direction (for example, the direction Q of FIG. 3)) in one direction (for example, the direction Q of FIG. 3), then turns back and extends only by the same length in the direction opposite to the one direction. The temperature adjustment heater 4 is disposed to meander such that the respective protruding parts are arranged at equal intervals. Likewise, the reaction flow path 3 is also disposed to meander such that the respective protruding parts are arranged at equal intervals. The protruding part of the reaction flow path 3 is disposed between the respective protruding parts of the temperature adjustment heater 4. That is, the reaction flow path 3 and the temperature adjustment heater 4 are arranged in a nested pattern such that each protruding part of the reaction flow path 3 is put into between the two sequent protruding parts of the temperature adjustment heater 4, and each protruding part of the temperature adjustment heater 4 is put into between the two sequent protruding parts of the reaction flow path 3. In this way, the temperature adjustment heater 4 can be disposed in the vicinity of the reaction flow path 3, so that the reaction flow path 3 can be uniformly and effectively heated by the temperature adjustment heater 4. The term "nested pattern" as used in the present invention means that each protruding part of the reaction flow path 3 is put into between the two sequent protruding parts of the temperature adjustment heater 4, and each protruding part of the temperature adjustment heater 4 is put into between the two sequent protruding parts of the reaction flow path 3.

As mentioned above, the first embodiment can provide the miniaturized microfluidic device 1 that has a simple structure without needing adhesion means for improving the heat transfer between the heater block and the device, and which can form the uniform temperature regions.

Second Embodiment

Figure 3:
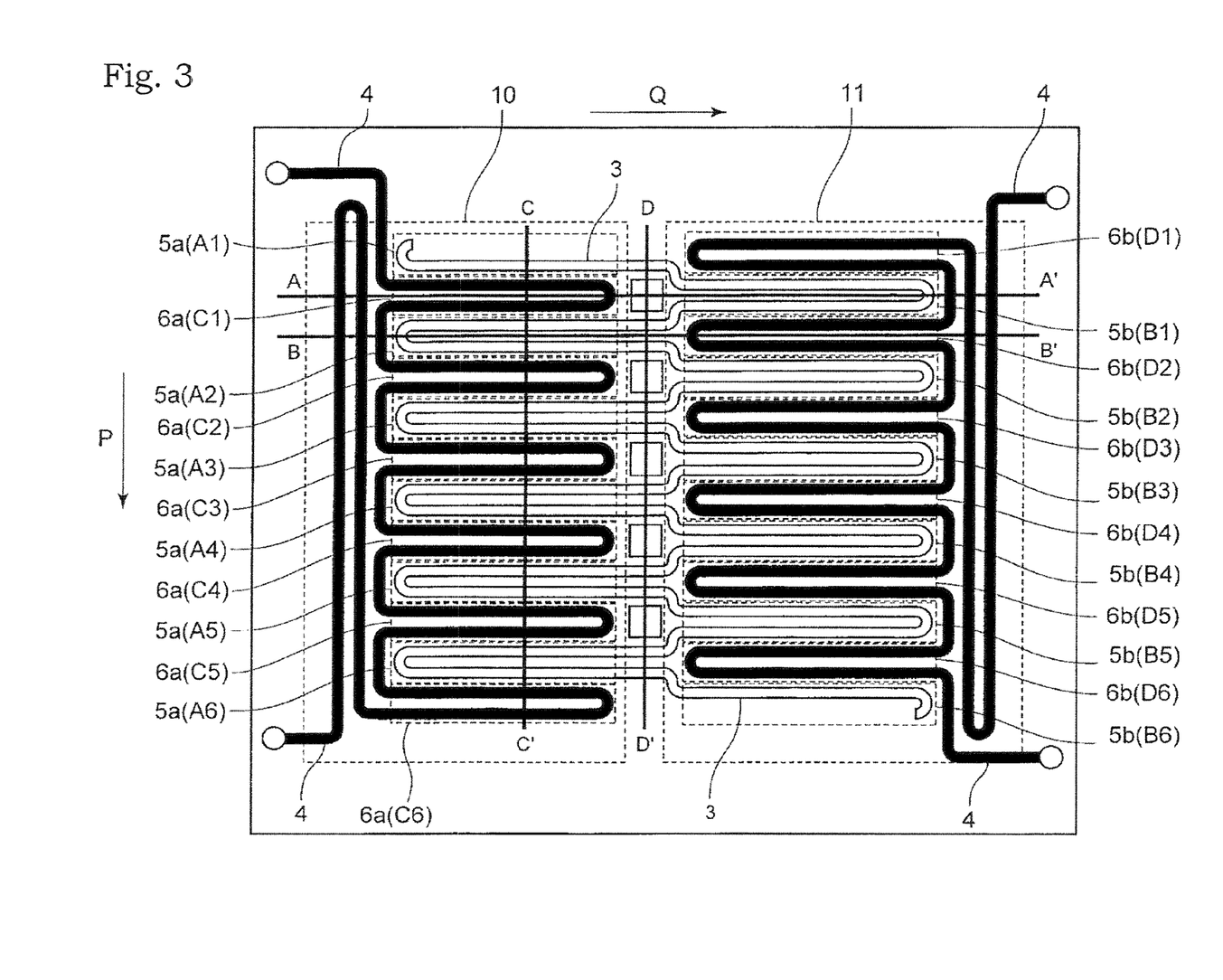
FIG. 3 is a top view of a substrate included in a microfluidic device according to a second embodiment of the invention.

FIG. 3 is a top view of a microfluidic device 1 according to a second embodiment of the invention in which temperature regions (first temperature region 10 and second temperature region 11) are arranged in two lines.

As shown in FIG. 3, the first temperature region 10 and the second temperature region 11 are formed over the microfluidic device 1. Each of the first and second temperature regions 10 and 11 is provided with the reaction flow path formation regions 5 and the temperature adjustment heater formation regions 6 which are alternately arranged in one direction P. The first temperature region 10 and the second temperature region 11 are arranged side by side in the direction different from one direction P, for example, in the direction Q substantially perpendicular to the one direction.

In the microfluidic device 1 of the second embodiment in the invention, as shown in FIG. 3, first reaction flow path formation regions 5a included in the first temperature region 10, and second reaction flow path formation regions 5b included in the second temperature region 11 may be alternately arranged. The reaction flow paths 3 formed in the first and second reaction flow path formation regions 5a and 5b which are disposed close to each other are preferably formed to communicate with each other. Thus, the protruding parts of the reaction flow path 3 can be alternately formed in the lateral direction with the line D-D' centered. That is, for example, odd-numbered protruding parts can be positioned on the left side, while even-numbered protruding parts can be positioned on the right side. In this way, each of the temperature adjustment heaters 4 can be formed to meander across the first temperature region 10 or the second temperature region 11. Since the first temperature region 10 and the second temperature region 11 can be set to different temperatures, the one reaction flow path 3 can be partially heated at different temperatures.

That is, the first temperature region 10 is formed by alternately arranging the first reaction flow path formation regions 5a and the first temperature adjustment heater formation regions 6a, whereas the second temperature region 11 is formed by alternately arranging the second reaction flow path formation regions 5b and the second temperature adjustment heater formation regions 6b. Thus, the first reaction flow path formation regions 5a included in the first temperature region 10 and the second reaction flow path formation regions 5b included in the second temperature region 11 are arranged in a staggered manner while being displaced from each other. The first reaction flow path formation regions 5a included in the first temperature region 10, and the second reaction flow path formation regions 5b included in the second temperature region 11, which are disposed close to each other, are arranged in a zig-zag manner. In more detail, as shown in FIG. 3, the first reaction flow path formation region 5a (A1) included in the first temperature region 10 is disposed close to the second reaction flow path region 5b (B1) included in the second temperature region 11, and the second reaction flow path formation region 5b (B1) included in the second temperature region 11 is disposed close to another first reaction flow path formation region 5a (A2) included in the first temperature region 10. Further, the first reaction flow path formation region 5a (A2) included in the first temperature region 10 is disposed close to the second reaction flow path formation region 5b (B2) included in the second temperature region 11, and the second reaction flow path formation region 5b (B2) included in the second temperature region 11 is disposed close to another first reaction flow path formation region 5a (A3) included in the first temperature region 10. Furthermore, the first reaction flow path formation region 5a (A3) included in the first temperature region 10 is disposed close to the second reaction flow path formation region 5b (B3) included in the second temperature region 11, and the second reaction flow path formation region 5b (B3) included in the second temperature region 11 is disposed close to another first reaction flow path formation region 5a (A4) included in the first temperature region 10. Moreover, the first reaction flow path formation region 5a (A4) included in the first temperature region 10 is disposed close to the second reaction flow path formation region 5b (B4) included in the second temperature region 11, and the second reaction flow path formation region 5b (B4) included in the second temperature region 11 is disposed close to another first reaction flow path formation region 5a (A5) included in the first temperature region 10. Still further, the first reaction flow path formation region 5a (A5) included in the first temperature region 10 is disposed close to the second reaction flow path formation region 5b (B5) included in the second temperature region 11, and the second reaction flow path formation region 5b (B5) included in the second temperature region 11 is disposed close to another first reaction flow path formation region 5a (A6) included in the first temperature region 10. Additionally, the first reaction flow path formation regions 5a (A6) included in the first temperature region 10 is disposed close to the second reaction flow path formation region 5b (B6) included in the second temperature region 11.

In the first temperature region 10, the temperature adjustment heaters 4 formed in the first temperature adjustment heater formation regions 6a disposed on both sides of and adjacent to the first reaction flow path formation region 5a in the one direction P are continuously formed, so that the one continuous temperature adjustment heater 4 and the one continuous reaction flow path 3 are formed in a nested pattern in the first temperature region 10. More specifically, as shown in FIG. 3, in the first temperature region 10, the temperature adjustment heater formation region 6a (C1) is formed between the reaction flow path formation regions 5a (A1) and 5a (A2), whereas the temperature adjustment heater formation region 6a (C2) is formed between the reaction flow path formation regions 5a (A2) and 5a (A3). The temperature adjustment heater formation region 6a (C3) is formed between the reaction flow path formation regions 5a (A3) and 5a (A4), whereas the temperature adjustment heater formation region 6a (C4) is formed between the reaction flow path formation regions 5a (A4) and 5a (A5). Likewise, the temperature adjustment heater formation region 6a (C5) is formed between the reaction flow path formation regions 5a (A5) and 5a (A6), whereas the temperature adjustment heater formation region 6a (C6) is formed adjacent to the reaction flow path formation regions 5a (A6) (adjacent in the one direction P (that is, in the positive direction on the P axis)). Thus, the temperature adjustment heaters 4 formed in the first temperature adjustment heater formation regions 6a (C1 to C6) are connected together to form the one continuous temperature adjustment heater 4 as shown in FIG. 3. In the first temperature region 10, the protruding parts on the left side of the one continuous temperature adjustment heater 4, and the protruding parts of the one continuous reaction flow path 3 are formed in a nested pattern.

Likewise, in the second temperature region 11, the temperature adjustment heaters 4 formed in the second temperature adjustment heater formation regions 6b disposed on both sides of and adjacent to the second reaction flow path formation region 5b in the one direction P are continuously formed, so that the one continuous temperature adjustment heater 4 is formed in the second temperature region 11. More specifically, as shown in FIG. 3, in the second temperature region 11, the temperature adjustment heater formation region 6b (D1) is formed adjacent to the reaction flow path formation region 5b (B1) (adjacent thereto in the direction opposite to the one direction P (negative direction on the P axis), whereas the temperature adjustment heater formation region 6b (D2) is formed between the reaction flow path formation regions 5b (B1) and 5b (B2). The temperature adjustment heater formation region 6b (D3) is formed between the reaction flow path formation regions 5b (B2) and 5b (B3), whereas the temperature adjustment heater formation region 6b (D4) is formed between the reaction flow path formation regions 5b (B3) and 5b (B4). Likewise, the temperature adjustment heater formation region 6b (D5) is formed between the reaction flow path formation regions 5b (B4) and 5b (B5), whereas the temperature adjustment heater formation region 6b (D6) is formed between the reaction flow path formation regions 5b (B5) and 5b (B6). Thus, as shown in FIG. 3, the temperature adjustment heaters 4 formed in the second temperature adjustment heater formation regions 6b (D1 to D6) are connected together to form the one continuous temperature adjustment heater 4. In the second temperature region 11, the protruding parts on the right side of the one continuous temperature adjustment heater 4, and the protruding parts of the one continuous reaction flow path 3 are formed in a nested pattern.

As shown in FIG. 3, in the first temperature region 10, the protruding parts of the reaction flow path 3 disposed meandering at equal intervals are arranged between the respective protruding parts of the temperature adjustment heater 4 disposed meandering at another equal interval, which can improve the uniform heat distribution. That is, the reaction flow path 3 and the temperature adjustment heater 4 are arranged in the nested pattern such that each protruding part of the reaction flow path 3 is put into the two sequent protruding parts of the temperature adjustment heater 4, and each protruding part of the temperature adjustment heater 4 is put into the two sequent protruding parts of the reaction flow path 3. Thus, the temperature adjustment heater 4 can be disposed in the vicinity of the reaction flow path 3, so that the reacting fluid can be effectively heated. The same goes for the second temperature region 11.

Figure 5:
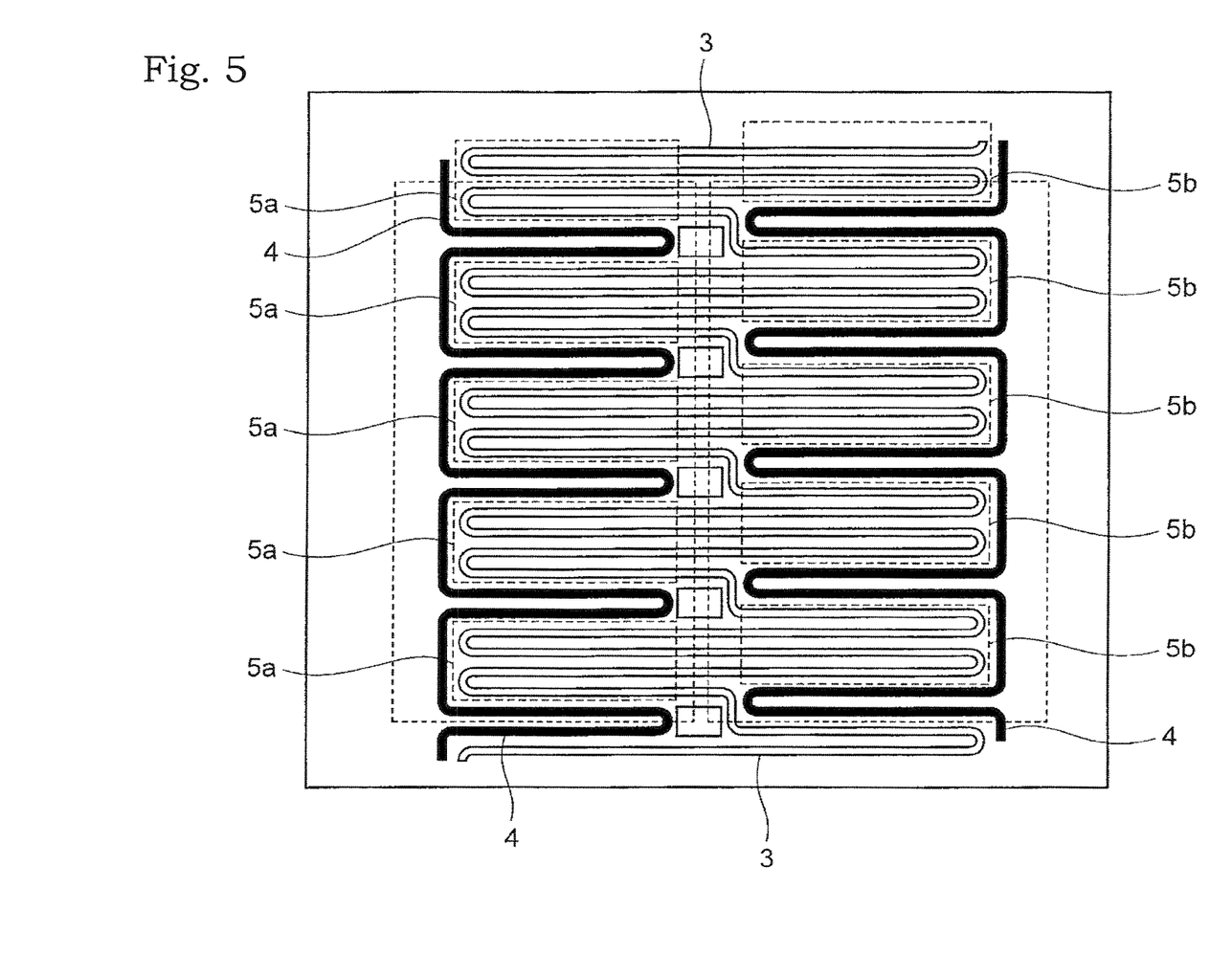
FIG. 5 is a top view of a microfluidic device according to another aspect of the second embodiment of the invention.
Figure 6:
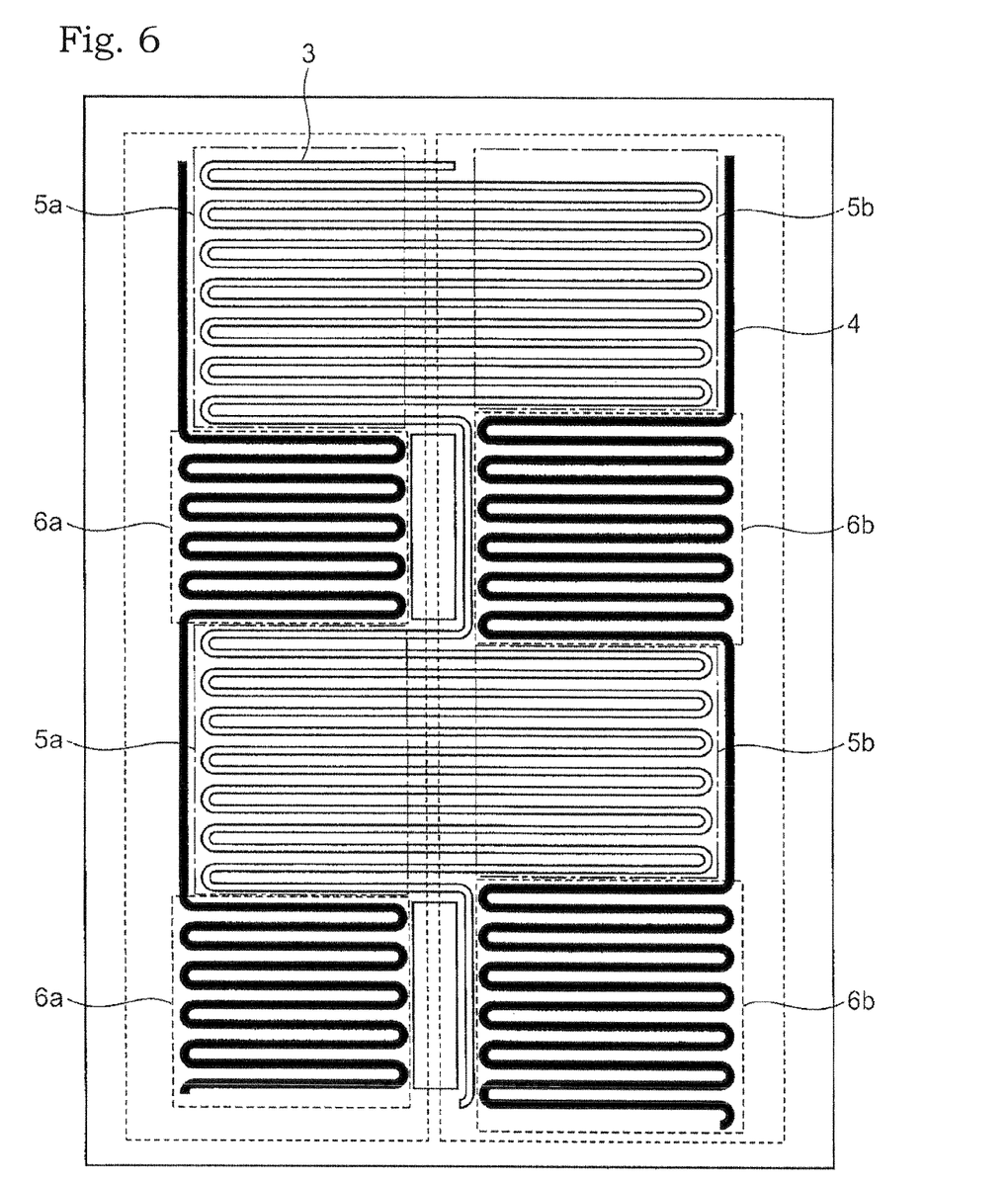
FIG. 6 is a top view of a microfluidic device according to a further aspect of the second embodiment of the invention.

Alternatively, as shown in FIG. 5, two protruding parts of the reaction flow path 3 may be provided in each reaction flow path formation region 5 (first reaction flow path formation region 5a, or second reaction flow path formation region 5b). Further, alternatively, as shown in FIG. 6, seven protruding parts of the reaction flow path 3 may be provided in each reaction flow path formation region 5. This arrangement can heat the reacting fluid at higher temperature, thereby achieving quick heating.

In the microfluidic device 1 of the second embodiment of the invention, the number of bending the temperature adjustment heater 4 in the one temperature adjustment heater formation region 6 preferably ranges from 1 to 50, and more preferably from 1 to 10. Setting of the number of bending the temperature adjustment heater 4 in such a range can achieve the uniform heating as well as the quick heating.

The microfluidic device 1 of the second embodiment in the invention, as shown in FIG. 1, preferably further includes a protective substrate 20 over the substrate 2. The reaction flow paths 3 formed in the substrate 2 to be opened outward, and the temperature adjustment heaters 4 arranged at the substrate 2 are covered with the protective substrate 20. This arrangement can protect the temperature adjustment heater 4, while preventing the leakage of the fluid inside the reaction flow path 3 from the reaction flow path 3.

The protective substrate 20 may be made of any other material that can surely protect the temperature adjustment heater 4 and the reaction flow path 3 formed on the substrate 2.

Figure 4A:
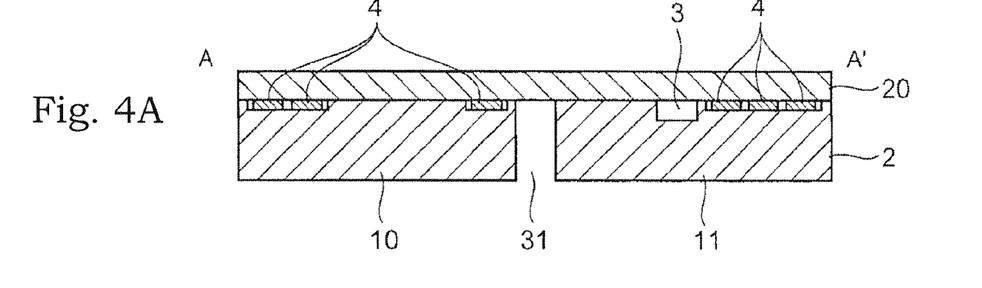
FIGS. 4A to 4D are cross-sectional views of the microfluidic device with an isolation trench at a boundary between two or more temperature regions in the second embodiment of the invention.
Figure 4B:
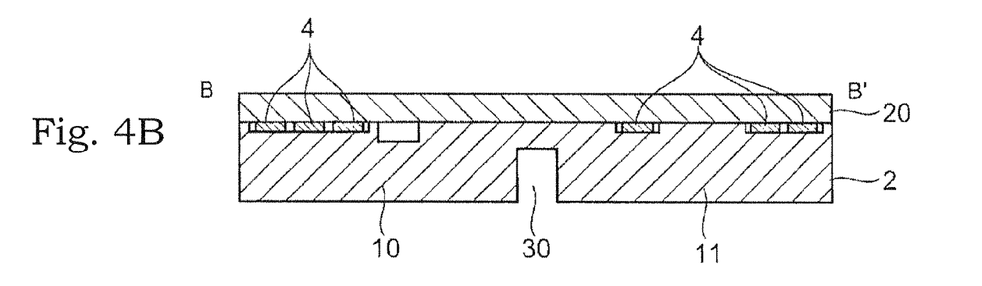
Figure 4C:
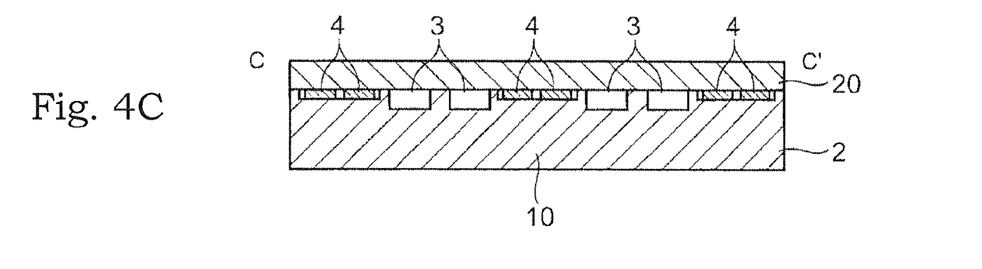
Figure 4D:
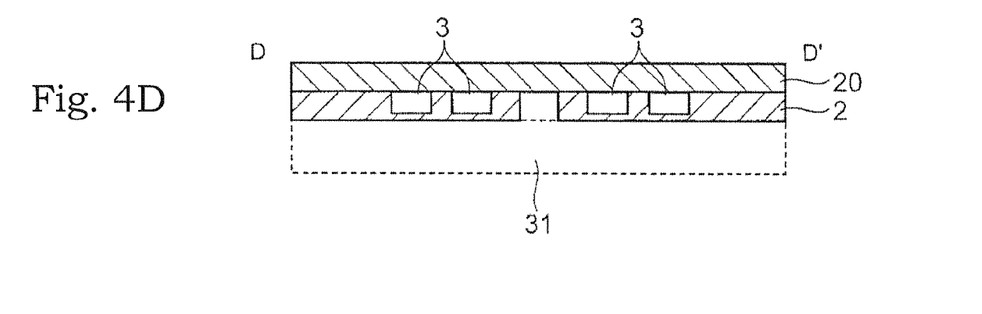

FIGS. 4A to 4D are cross-sectional views of the microfluidic device 1 with an isolation trench at a boundary between two or more temperature regions in the second embodiment of the invention. FIG. 4A is the cross-sectional view of the microfluidic device 1 taken along the line A-A' of FIG. 3, and FIG. 4B is the cross-sectional view of the microfluidic device 1 taken along the line B-B' of FIG. 3. FIG. 4C is the cross-sectional view of the microfluidic device 1 taken along the line C-C' of FIG. 3, and FIG. 4D is the cross-sectional view of the microfluidic device 1 taken along the line D-D' of FIG. 3.

As shown in FIG. 4B, an isolation trench 30 may be formed at the boundary between two or more temperature regions 10 and 11 to be opened toward the back surface of the substrate 2. The two temperature regions 10 and 11, as shown in FIG. 4B, may be connected together by a part other than the isolation trench 30. The isolation trench 3C is to improve thermal insulation between the temperature regions. Thus, the isolation trench 30 is formed at the boundary between the two or more temperature regions as mentioned above, which can improve thermal insulation between the temperature regions 10 and 11. The isolation trench 30 may have any other sectional shape as long as the thermal insulation between the temperature regions 10 and 11 is improved. The sectional shape of the isolation trench 30 is preferably rectangular as the isolation trench 30 can be easily formed. The isolation trench 30 is to improve the thermal insulation between the temperature regions 10 and 11, and thus is not necessarily opened at the back surface of the substrate 2. Further, the isolation trench 30 may not be opened on both the front and back surfaces of the substrate 2 (in other words, a closed space may be formed between the temperature regions 10 and 11 of the substrate 2). Even with both the front and back surfaces of the substrate 2 closed, the thermal insulation between the temperature regions 10 and 11 can be surely improved.

In the microfluidic device 1 of the first embodiment in the invention, as shown in FIGS. 4A and 4D, a through hole 31 may be further provided to penetrate the substrate 2 from the back surface to front surface thereof at the boundary between the two temperature regions 10 and 11. This arrangement can further improve the thermal insulation between the temperature regions 10 and 11.

As shown in FIGS. 4A, 4B, and 4C, in the microfluidic device 1 of the first embodiment in the invention, preferably, a stepped portion is formed between the surface with the temperature adjustment heater 4 formed thereon and the uppermost surface of the substrate 2, which prevents the temperature adjustment heater 4 from protruding from the uppermost surface of the substrate 2. With this arrangement, the protective substrate 20 can be easily bonded to the substrate 2 to thereby improve the yield of the devices.

In the microfluidic device 1 according to the first embodiment of the invention, the temperature adjustment heater 4 is preferably a metal thin film heater. The temperature adjustment heater 4 made of the metal thin film heater can be easily integrated on the device.

Suitable materials used for the metal thin film heater can include metals, for example, gold, platinum, copper, aluminum, and the like. These materials can be suitably used because of low resistance and good workability.

Methods for forming the metal thin film heater can be the well-known methods, including sputtering, vapor deposition, and the like.

In the microfluidic device 1 according to the first embodiment of the invention, the temperatures of the two or more temperature adjustment heaters 4 can be preferably adjusted independently. The two or more temperature adjustment heaters 4 can have the temperature thereof adjusted independently, which can achieve the temperature control with high accuracy.

As mentioned above, the second embodiment can provide the miniaturized microfluidic device 1 with the heater that has a simple structure without needing adhesion means for improving the heat transfer between the heater block and the device, and which can form the uniform temperature regions. The two or more temperature regions with different temperatures can be formed to thereby adjust the fluid in the reaction flow path 3 to various temperatures, which can provide the microfluidic device with good temperature controllability.

Third Embodiment

Figure 7:
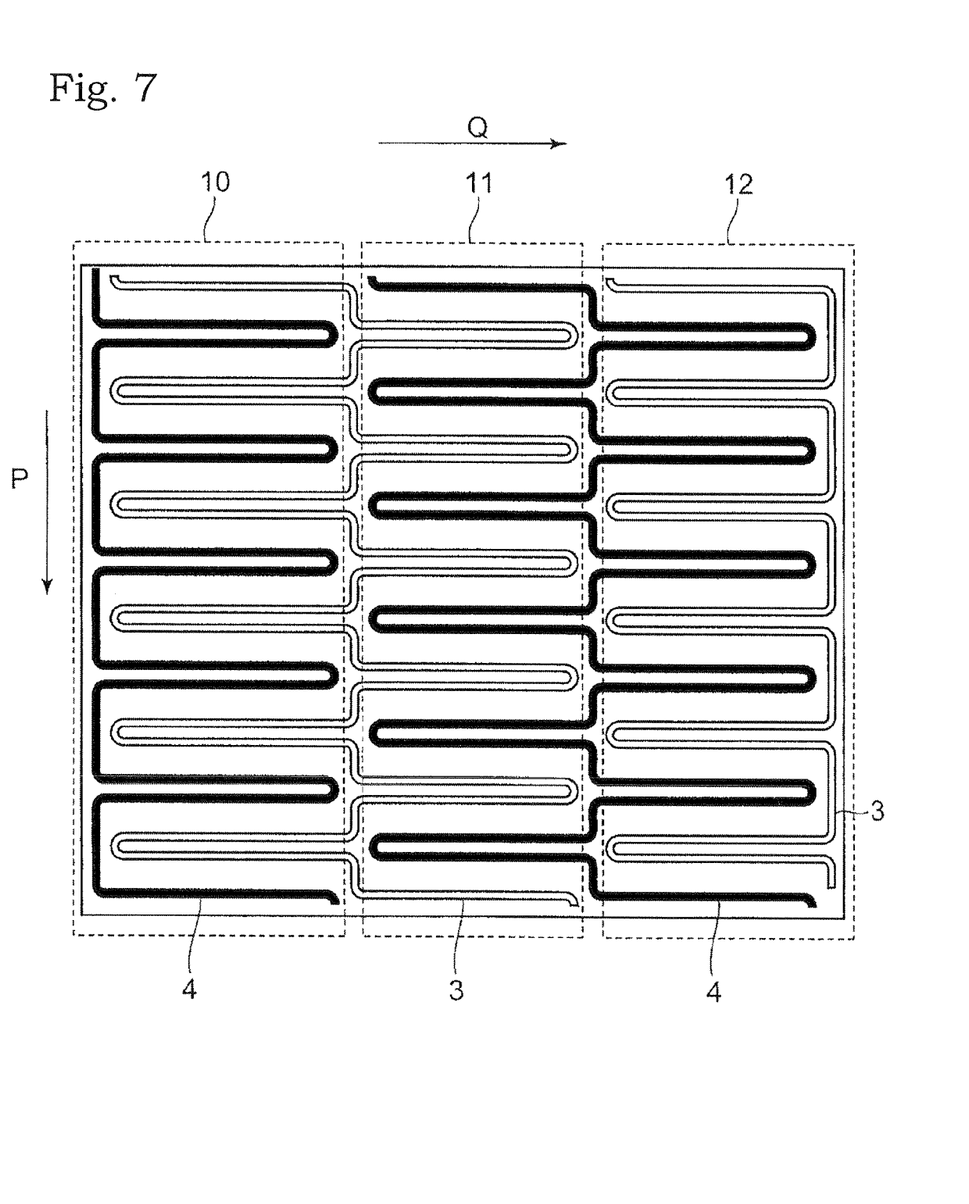
FIG. 7 is a top view of a microfluidic device according to a third embodiment of the invention.

FIG. 7 is a top view of a microfluidic device 1 according to a third embodiment of the invention in which temperature regions (first temperature region 10, second temperature region 11, and third temperature region 12) are arranged side by side in three lines. While in the second embodiment, the temperature regions are arranged side by side in two lines, in the third embodiment, the temperature regions are arranged side by side in three lines, which is the different point between the second and third embodiments. This embodiment is the same as the first and second embodiments except for the above-mentioned point.

As shown in FIG. 7, the first temperature region 10, the second temperature region 11, and the third temperature region 12 are formed at the microfluidic device 1. In each of the first, second, and third temperature regions 10, 11, and 12, the reaction flow path formation regions 5 and the temperature adjustment heater formation regions 6 are alternately arranged in the one direction P. The first temperature region 10, second temperature region 11, and third temperature region 12 are arranged side by side in the direction different from the one direction P, for example, in the direction Q substantially perpendicular to the one direction.

In the microfluidic device 1 according to the third embodiment of the invention, first reaction flow path formation regions 5a included in the first temperature region 10, and second reaction flow path formation regions 5b included in the second temperature region 11 are arranged in a staggered manner. The reaction flow paths 3 formed in the first and second reaction flow path formation regions 5a and 5b which are disposed close to each other are preferably formed to communicate with each other to thereby form one continuous reaction flow path 3 over the first and second temperature regions 10 and 11.

Further, second temperature adjustment heater formation regions 6b included in the second temperature region 11, and third temperature adjustment heater formation regions 6c included in the third temperature region 12 are arranged in a staggered manner. The temperature adjustment heaters 4 formed in the second and third temperature adjustment heater formation regions 6b and 6c which are disposed close to each other are continuously formed to thereby form one continuous temperature adjustment heater 4 across the second and third temperature regions 11 and 12.

In the first temperature region 10, the temperature adjustment heaters 4 formed in the first temperature adjustment heater formation regions 6a disposed on both sides of and adjacent to the first reaction flow path formation region 5a are continuously formed, so that the one continuous temperature adjustment heater 4 is formed in the first temperature region 10.

Likewise, in the third temperature region 12, the reaction flow paths 3 formed in the third reaction flow path formation regions 5 disposed on both sides of and adjacent to the third temperature adjustment heater formation region 6 are formed to communicate with each other, so that the one continuous reaction flow path 3 is formed in the third temperature region 12.

In this way, the microfluidic device 1 with the temperature regions arranged side by side in three lines can be manufactured. The number of the reaction flow paths 3 and/or temperature adjustment heaters 4 each continuously formed across the two temperature regions can be increased to form four or more lines of the temperature regions.

Alternatively, in the microfluidic device 1 according to the third embodiment, the temperature adjustment heater 4 formed in one temperature adjustment heater formation region 6 that is included in each of the first temperature region 10, the second temperature region 11, and the third temperature region 12 may be bent twice or more. This can enhance the reaction efficiency of the fluid (reactive material or the like) in the reaction flow path 3.

Further, in the microfluidic device 1 according to the third embodiment, the reaction flow path 3 formed in one reaction flow path formation region 5 that is included in each of the first temperature region 10, the second temperature region 11, and the third temperature region 12 may be bent twice or more.

As mentioned above, the third embodiment can provide the miniaturized microfluidic device 1 with the heater that has a simple structure without needing adhesion means for improving the heat transfer between the heater block and the device, and which can form the uniform temperature regions. The three or more temperature regions with different temperatures can be formed to thereby adjust the fluid in the reaction flow path 3 to various temperatures, which can provide the microfluidic device with good temperature controllability.

The device of the invention can be applied to a polymerase chain reaction (PCR) device. The PCR method is a reaction for amplifying the number of deoxyribonucleic acid (DNA) molecules. Specifically, the PCR involves causing a reactive solution containing DNA segments to be amplified, polymerase enzyme, and primers to undergo about 30 to 50 repeated cycles of temperature changes, including a denaturation temperature (about 95° C.), an anneal temperature (about 60° C.), and an extension temperature (from about 60° C. to about 75° C.), thereby exponentially amplifying the DNA template.

The high-temperature region (for example, from 95° C. to 98° C.) for carrying out the degeneration reaction, and the low-temperature regions (for example, from 50° C. to 75° C.) for carrying out the anneal and extension reactions are formed by the heater. Here, the anneal reaction and the extension reaction are carried out at the same temperature in the description. However, these reactions may be performed at different temperatures with different temperature regions formed independently. The time during which the DNA stays in each temperature region is controlling by adjusting the velocity of the reacting fluid. According to the present invention, the temperatures of the temperature regions can be uniformly controlled, so that each reaction can be repeatedly carried out at the same corresponding temperature in all PCR cycles, which can achieve very effective and excellent amplification of the DNA.

DESCRIPTION OF REFERENCE NUMERALS

1 Microfluidic device
2 Substrate
3 Reaction flow path
4 Temperature adjustment heater
5 Reaction flow path formation region
5a First reaction flow path formation region
5b Second reaction flow path formation region
6 Temperature adjustment heater formation region
6a First temperature adjustment heater formation region
6b Second temperature adjustment heater formation region
10 First temperature region
11 Second temperature region
12 Third temperature region

The invention claimed is:
1. A microfluidic device, comprising:
a substrate;
a reaction flow path formed on the substrate; and
a temperature adjustment heater for heating the reaction flow path,
wherein a reaction flow path formation region including the reaction flow path formed therein and a temperature adjustment heater formation region including the temperature adjustment heater formed therein are alternately arranged on the substrate,
the reaction flow path is formed to be bent at least one time in the reaction flow path formation region, and
the temperature adjustment heater is formed to be bent at least one time in the temperature adjustment heater formation region.

2. The microfluidic device according to claim 1, further comprising a first temperature region and a second temperature region, each having the reaction flow path formation region and the temperature adjustment heater formation region being alternately arranged in one direction therein,
wherein the first temperature region and the second temperature region are arranged side by side in a direction different from the one direction.

3. The microfluidic device according to claim 2, wherein a first reaction flow path formation region included in the first temperature region and a second reaction flow path formation region included in the second temperature region are arranged in a staggered manner, and
the reaction flow paths respectively formed in the first reaction flow path formation region and in the second reaction flow path formation region being located close to each other are formed to communicate with each other.

4. The microfluidic device according to claim 2, wherein a first temperature adjustment heater formation region included in the first temperature region and a second temperature adjustment heater formation region included in the second temperature region are arranged in a staggered manner, and the temperature adjustment heaters respectively formed in the first temperature adjustment heater formation region and in the second temperature adjustment heater formation region being located close to each other are continuously formed.

5. The microfluidic device according to claim 1, wherein two or more temperature adjustment heaters each being bent to meander are disposed in the one temperature adjustment heater formation region.

6. The microfluidic device according to claim 1, wherein two or more reaction flow paths each being bent to meander and separated are disposed in the one reaction flow path formation region.

7. The microfluidic device according to claim 1, wherein the number of bending the temperature adjustment heater in the one temperature adjustment heater formation region ranges from 1 to 10.

8. The microfluidic device according to claim 1, wherein the number of bending the reaction flow path in the one reaction flow path formation region ranges from 1 to 10.

9. The microfluidic device according to claim 1, further comprising a protective substrate over the substrate, wherein the reaction flow path formed in the substrate to be opened outward, and the temperature adjustment heater disposed in the substrate are covered with the protective substrate.

10. The microfluidic device according to claim 2, further comprising an isolation trench formed at a boundary between the two or more temperature regions.

11. The microfluidic device according to claim 10, further comprising a through hole to penetrate the substrate from the back surface to a front surface thereof at the boundary.

12. The microfluidic device according to claim 1, wherein a stepped portion is formed between a surface with the temperature adjustment heater formed thereon and the front surface of the substrate, so that the temperature adjustment heater does not protrude from the front surface of the substrate.

13. The microfluidic device according to claim 1, wherein the temperature adjustment heater is a metal thin film heater.

14. The microfluidic device according to claim 5, wherein the temperatures of the two or more temperature adjustment heaters are adjustable independently.

15. A polymerase chain reaction device comprising the microfluidic device according to claim 1.

* * * * *